(12) United States Patent
Duclos et al.

(10) Patent No.: US 6,496,250 B1
(45) Date of Patent: Dec. 17, 2002

(54) COMBINATORIAL METHOD FOE DEVELOPMENT OF OPTICAL CERAMICS

(75) Inventors: Steven Jude Duclos, Clifton Park, NY (US); Charles David Greskovich, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 69 days.

(21) Appl. No.: 09/677,450

(22) Filed: Sep. 29, 2000

(51) Int. Cl.⁷ .................................................. G01N 1/00
(52) U.S. Cl. ........................................................ 356/36
(58) Field of Search ...................... 356/36, 38; 436/85, 436/149, 157, 170, 174, 501, 510

(56) References Cited

U.S. PATENT DOCUMENTS

| | | | |
|---|---|---|---|
| 4,242,221 A | 12/1980 | Cusano et al. | 252/301 |
| 4,421,671 A | 12/1983 | Cusano et al. | 252/301 |
| 4,442,360 A | 4/1984 | Suzuki et al. | 250/486 |
| 4,466,929 A | 8/1984 | Greskovich et al. | 264/1.2 |
| 4,466,930 A | 8/1984 | Greskovich et al. | 264/1.2 |
| 4,473,412 A | 9/1984 | Nathasingh et al. | 148/31.5 |
| 4,518,545 A | 5/1985 | Cusano et al. | 264/1.2 |
| 4,518,546 A | 5/1985 | Greskovich et al. | 264/1.2 |
| 4,525,628 A | 6/1985 | DiBianca et al. | 250/367 |
| 4,571,312 A | 2/1986 | Greskovich et al. | 264/1.2 |
| 4,747,973 A | 5/1988 | Cusano et al. | 252/301.4 |
| 4,783,596 A | 11/1988 | Riedner et al. | 250/483 |
| 5,143,854 A | 9/1992 | Pirrung et al. | 436/518 |
| 5,424,186 A | 6/1995 | Fodor et al. | 435/6 |
| 5,484,750 A | 1/1996 | Greskovich et al. | 501/86 |
| 5,985,356 A | 11/1999 | Schultz et al. | 427/8 |
| 6,346,290 B1 * | 2/2002 | Schultz et al. | 427/8 |

FOREIGN PATENT DOCUMENTS

WO          WO 92/10092          6/1992

* cited by examiner

Primary Examiner—Michael P. Stafira
(74) Attorney, Agent, or Firm—Toan P. Vo; Noreen C. Johnson

(57) ABSTRACT

A method of preparing and testing an array of ceramics for optical properties, comprising: providing a host material that is capable of being made optically transparent or translucent upon sintering; forming the host material into an array of pixels attached to a base plate; doping the host material; reacting the host material and the dopant, to form an array of products; and testing the products for optical properties.

36 Claims, 2 Drawing Sheets

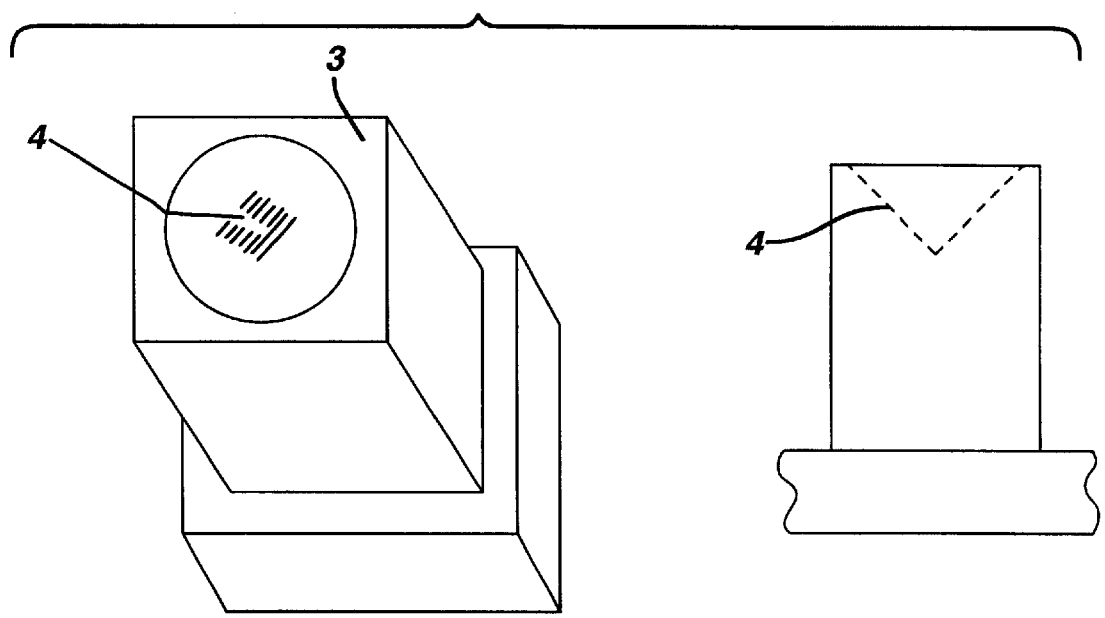

COMBINATORIAL METHOD FOE DEVELOPMENT OF OPTICAL CERAMICS

BACKGROUND OF THE INVENTION

1. Field of the Invention

This invention relates to a method for screening transparent materials, and more particularly to a combinatorial method for screening an array of transparent materials.

2. Description of Related Art

Combinatorial chemistry techniques have been developed by the pharmacutical industry for the rapid development and screening of drug chemistries. For example, Pirrung et al. developed a technique for generating arrays of peptides and other molecules using, for example, light-directed, spatially-addressable synthesis techniques (U.S. Pat. No. 5,143,854). In addition, Fodor et al. have developed automated techniques for performing light-directed, spatially-addressable synthesis techniques, photosensitive protecting groups, masking techniques and methods for gathering fluorescence intensity data (Fodor et al., PCT Publication No. WO 92/10092).

Using these various methods of combinatorial synthesis, arrays containing thousands or millions of different organic elements can be formed (U.S. Pat. No. 5,424,186). The solid phase synthesis techniques currently being used to prepare such libraries involve a stepwise process (i.e., sequential, coupling of building blocks to form the compounds of interest). In the Pirrung et al. method, for example, polypeptide arrays are synthesized on a base material by attaching photoremovable groups to the surface of the base material, exposing selected regions of the base material to light to activate those regions, attaching an amino acid monomer with a photoremovable group to the activated region, and repeating the steps of activation and attachment until polypeptides of the desired length and sequences are synthesized. The Pirrung et al. method is a sequential, step-wise process utilizing attachment, masking, deprotecting, attachment, etc. Such techniques have been used to generate libraries of biological polymers and small organic molecules to screen for their ability to specifically bind and block biological receptors (i.e., protein, DNA, etc.). These solid phase synthesis techniques, which involve the sequential addition of building blocks (i.e., monomers, amino acids) to form the compounds of interest, cannot readily be used to prepare many inorganic and organic compounds. As a result of their relationship to semiconductor fabrication techniques, these methods have come to be referred to as "Very Large Scale Immobilized Polymer Synthesis," or "VLSIPS" technology. Robotics are used to mix and process hundreds or thousands of samples simultaneously, allowing for parallel testing of material mixtures for efficacy.

More recently combinatorial techniques have been applied to inorganic materials in the form of thin films deposited or evaporated onto a substrate. For example, Schultz et al. applied combinatorial chemistry techniques to the field of material science in U.S. Pat. No. 5,985,356. More particularly, Schultz et al. disclosed methods and apparatus for the preparation and use of a substrate having thereon an array of diverse materials in predefined regions. An appropriate array of materials is generally prepared by delivering components of materials to predefined regions on the substrate and simultaneously reacting the reactants to form different materials. While these films have known composition, the particle size and porosity of the material make it highly scattering and non-transparent.

A luminescent material absorbs energy in one portion of the electromagnetic spectrum and emits energy in another portion of the electromagnetic spectrum. A luminescent material in powder form, where the material is excited by UV light to generate photons is commonly called a phosphor, while a luminescent material in the form of a transparent solid body that is excited by gamma or X-rays to generate visible photons is commonly called a scintillator.

Most useful phosphors emit radiation in the visible portion of the spectrum in response to the absorption of the radiation which is outside the visible portion of the spectrum. Thus, the phosphor performs the function of converting electromagnetic radiation to which the human eye is not sensitive into electromagnetic radiation to which the human eye is sensitive. Most phosphors are responsive to more energetic portions of the electromagnetic spectrum than the visible portion of the spectrum. Thus, there are powder phosphors which are responsive to ultraviolet light (as in fluorescent lamps), electrons (as in cathode ray tubes) and x-rays (as in radiography).

There are a number of known scintillators each of which has its own set of properties such as the turn-on delay, efficiency, primary decay time, afterglow, hysteresis, luminescent spectrum, radiation damage and so forth. The turn-on delay of a luminescent material is the time period between the initial impingement of stimulating radiation on the luminescent material and the luminescent output reaching its maximum value, for a constant intensity of stimulating radiation. The efficiency of a luminescent material is the percentage of the energy of the absorbed stimulating radiation which is emitted as luminescent light. When the stimulating radiation is terminated, the luminescent output from a scintillator decreases in two stages. The first of these stages is a rapid decay from the full luminescent output to a low, but normally non-zero, value at which the slope of the decay changes to a substantially slower decay rate. This low intensity, normally long decay time luminescence, is known as afterglow and usually occurs with intensity values less than 2% of the full intensity value. The initial, rapid decay is known as the primary decay or primary speed and is measured from the time at which the stimulating radiation ceases to the time at which the luminescent output falls to 1/e of its full intensity value.

A luminescent material exhibits hysteresis if the amount of luminescent light output for a given amount of incident stimulating radiation depends upon the amount of stimulating radiation which has been recently absorbed by the luminescent material. The luminescent spectrum of a luminescent material is the spectral characteristics of the luminescent light which is emitted by that material.

Radiation damage is the characteristic of a luminescent material in which the quantity of light emitted by the luminescent material in response to a given intensity of stimulating radiation changes after the material has been exposed to a high radiation dose. Radiation damage may be measured by first stimulating a luminescent material with a known, standard or reference, intensity of radiation. The initial output ($I_o$) of the photodetector in response to this reference intensity of incident stimulating radiation is measured and recorded or stored. Next, the luminescent material is exposed to a high dosage of radiation. Finally, the luminescent material is immediately again exposed to the reference intensity of stimulating radiation and the final output ($I_f$) of its photodetector, in response to this reference intensity of stimulating radiation, is measured and stored or recorded. The radiation damage (RD) may then be expressed as:

$$RD = \frac{I_f - I_o}{I_o}$$

Ideally, the radiation damage should be as small as possible. In most luminescent materials, it is a negative number because it is normally less than $I_o$.

In a computed tomography (CT) scanning system, an x-ray source and an x-ray detector array are positioned on opposite sides of the subject and rotated around the subject in fixed relation to each other. CT scanners with solid scintillators are known in the art. In a solid scintillator system, the scintillator material of a cell or element absorbs x-rays incident on that cell and emits light which is collected by a photodetector for that cell. During data collection, each cell or element of the detector array provides an output signal representative of the present light intensity in that cell of the array. These output signals are processed to create an image of the subject in a manner which is well known in the CT scanner art. It is desirable for the luminescent material in a CT scanner to have a linear characteristic in which the light output is a linear function of the amount of stimulating radiation which is absorbed in order that light output may be directly converted to a corresponding intensity of stimulating radiation in a linear manner.

In systems such as CT scanners, the luminescent material has many specialized characteristics which are not needed in many of the previously mentioned phosphor based systems. First, in x-ray based CT systems, it is desirable to absorb substantially all of the incident x-rays in the luminescent material in order to minimize the x-ray dose to which the patient must be exposed in order to obtain the computed tomography image. In order to collect substantially all of the incident x-rays, the luminescent material must have a thickness in the direction of x-ray travel which is sufficient to stop substantially all of the x-rays. This thickness depends both on the energy of the x-rays and on the x-ray stopping power of the luminescent material. Second, it is important that substantially all of the luminescent light be collected by the photosensitive detector in order to maximize overall system efficiency, the signal-to-noise ratio and the accuracy with which the quantity of incident stimulating radiation may be measured. In order to extract substantially all of the luminescent light generated in the luminescent material of the CT scanner, the luminescent material should be. transparent to the luminescent light. Otherwise much of the luminescent light will not reach the photosensitive detector because of scattering and absorption within the luminescent material. Consequently, the luminescent material is provided in the form of a solid bar which is substantially transparent to the luminescent light and which is thick enough in the direction of x-ray travel to absorb substantially all of the incident x-rays. This complicates both the selection of a luminescent material for use in CT scanning and its preparation since many materials which are known to luminesce and which have been used or tested as powder phosphors cannot be provided in the form of a solid bar having the necessary transparency.

The luminescent properties of materials have not been tabulated in handbooks in the manner in which the melting point, boiling point, density and other more mundane physical characteristics of various compounds have been tabulated. Most luminescent data is found in articles with respect to particular materials which the authors have measured for one reason or another. Further, most characterization of luminescent materials has been done using ultraviolet (UV) light as the stimulating radiation because ultraviolet light is more easily produced than x-rays and is generally considered less harmful. Unfortunately, there are a number of materials which are luminescent in response to ultraviolet light stimulation which are not luminescent in response to x-ray stimulation. Consequently, for many materials, even that luminescent data which is available provides no assurance that the material will luminesce in response to x-ray stimulation. Further, for many applications of phosphors many of the parameters which must be closely controlled in a scintillator for use in a state-of-the-art CT scanning system are unimportant and thus have not been measured or reported. Consequently, existing luminescent material data provides little, if any, guidance in the search for a scintillator material appropriate for use in a state-of-the-art CT scanning system. Among the parameters on which data is generally unavailable are radiation damage in response to x-ray stimulation, afterglow, susceptibility to production in single crystalline form, hysteresis phenomena, mechanical quality and in many cases, even whether they are x-ray luminescent. The large number of parameters which must meet strict specifications in order for a given material to be suitable for use in a state-of-the-art CT scanner, including the ability to provide the material in the form of transparent scintillator bodies, makes the process of identifying a suitable scintillator material one which essentially begins from scratch and is akin to searching for "a needle in a haystack".

There are several reasons that it is desirable that the radiation damage be as small as possible. One disadvantage of high radiation damage is that as radiation damage accumulates, the sensitivity of the system decreases because of the progressively smaller quantity of light which is emitted by the scintillator material for a given stimulating dosage of radiation. Another disadvantage is that for too high a radiation damage, the scintillation detectors must eventually be replaced because of the cumulative effects of the radiation damage. This results in a substantial capital cost for the replacement of the scintillation detecting system. A more bothersome, and potentially even more expensive effect of high radiation damage is a need to recalibrate the system frequently during the working day, and potentially as frequently as after every patient. Such recalibration takes time and also exposes the scintillator material to additional radiation which contributes further damage. It is considered desirable that the radiation damage of a scintillator material for use in a CT scanning system be small enough that calibration of the system at the beginning of each working day is sufficient to ensure accurate results throughout the working day.

One way of providing the luminescent material in the form of a transparent bar is to employ a single crystalline luminescent material which is transparent to its own luminescent radiation. A common method of growing single crystals is the Czochralski growth technique in which appropriate source materials are placed in a high temperature crucible which is often made of iridium (Ir) and the crucible and its contents are heated to above the melting point of the desired single crystalline material. The resulting molten material is known as the melt. During growth, the melt temperature is held at a value at which the upper portion of the melt is cool enough for single crystalline material to grow on a seed crystal brought into contact with the melt, but not to spontaneously nucleate. A seed crystal of the desired material or one on which the desired material will grow as a single crystal is lowered into contact with the top of the melt. As the desired crystalline material grows on the seed crystal, the seed crystal is withdrawn (pulled upward) at a rate which maintains the growing boule of single crystalline material at a desired diameter. Typically, the seed crystal is rotated during growth to enhance the uniformity of the growing crystal. The source material which is initially placed in the crucible may take any appropriate form, but is normally a mixture of appropriate quantities of source materials which together provide a melt having the stoichiometry and impurity control desired for the single crystalline material to be grown.

When a pure crystal is grown from a corresponding melt, the Czochralski growth technique normally provides a high quality, uniform composition single crystal of the desired composition. When it is desired to produce a crystal having substitutions for some portion of the atoms of the pure crystalline material, the growth dynamics are more complex and the manner in which the substituent enters into the crystal structure and thus its concentration in the melt and boule as functions of time depend on a number of characteristics. One of the effects of these characteristics is characterized as the segregation coefficient. The segregation coefficient has a value of 1 when the substituent is normally present in the solid boule in the same ratio as it is present in the source melt. The segregation coefficient is greater than 1 when the substituent is normally present in the solid boule in greater concentration than it is present in the source melt and the segregation coefficient is less than 1 when the substituent is normally present in the solid boule in lesser concentrations than it is present in the melt. While there are a number of different fundamental reasons for these differences, the segregation coefficient is an effective means of expressing the result.

In a CT scanning system, one of the important characteristics of a scintillator bar is its Z-axis response curves. Individual scintillator bars are normally narrow for maximum resolution and deeper than wide to provide adequate x-ray stopping power and relatively long perpendicular to the plane of the x-ray beam/scintillator system in order to collect sufficient x-rays to be efficient. The Z-axis characteristic is the photodetector output in response to a constant intensity, narrow, x-ray stimulating beam as that beam is scanned from one Z-direction end of the scintillator bar to the other. Ideally, this characteristic is symmetric about the longitudinal center of the scintillator bar and increases monotonically from each end to the center. The increase in output near the ends of the bar is preferably complete once the entire Z-direction thickness of the beam is disposed on the scintillator bar with the output being substantially uniform along the intervening portion of the bar.

In order to meet these Z-axis requirements, the scintillator bar should have substantially uniform optical, luminescent and source radiation absorption properties along its entire length. For single crystal, impurity-activated scintillator bars, this requires the ability to grow source boules having uniform luminescent activator concentration both radially and lengthwise of the boule, since the luminescent output is dependent on the local concentration of the activator ion. Consequently, the process of selecting a scintillator material for a CT scanner, in addition to determining all of the other important properties of the material, preferably also includes establishing the feasibility of producing scintillator bars with acceptable Z-axis characteristics.

In a CT scanner, it is preferable to provide a reflective surface on all surfaces of the scintillator bar other than the surface along which the photodetector diode is disposed. Thus, a typical solid scintillation detector system comprises a plurality of individual scintillator bars positioned side-by-side with an individual photodetector diode coupled to each scintillator bar to convert its luminescent light into a corresponding electrical signal. It is important in such a system that all of the scintillator bars have similar overall conversion efficiencies (that is, substantially identical electrical output signals for identical incident x-ray radiation). This places another limitation on the selection of the scintillator material in that it must be possible to produce a sufficient quantity of scintillator bars having similar characteristics to assemble a scintillation detector having as many as 1,000 or more elements.

The primary decay time determines how fast a CT scanner can scan a patient since it is necessary for the luminescent output in response to radiation incident in one position of the scanner to have ceased before the luminescent output at another position of the scanner can be accurately measured. At present, a primary decay time of less than 500 microseconds is preferred, with still lower values being more desirable if they can be obtained without undesirable effects on other properties of the scintillator material such as maximum light output, radiation damage and hysteresis. It is also desirable that the maximum afterglow level be very small and that it decay relatively rapidly. For modern CT scanners, afterglow may be measured at 100 to 150 milliseconds after stimulating radiation termination and again at 300 milliseconds to characterize a scintillator material. An afterglow of less than 0.1% is considered highly desirable since the photodetector cannot distinguish between luminescent light which is a result of afterglow from earlier stimulation and luminescent light which is a result of present stimulation. Thus, afterglow can limit the intensity resolution of a CT scanner system.

For purposes of comparing the efficiency of different candidate scintillator materials, it is convenient to normalize light output. The amplitude of the output signal from a photodetector diode in response to stimulation of a standard sized scintillator bar of the candidate material with an established reference intensity of x-rays is compared with the output produced by cadmium tungstate of the same configuration in response to the same stimulation. Cadmium tungstate is a convenient standard because the self-activated nature of its luminescence results in substantially fixed light output for a given intensity of stimulating radiation so long as it has not been heavily radiation damaged, since its light output does not depend on the concentration of an activator. Thus, light output data taken by different individuals and at different times can be directly compared without having to first establish the calibration of different test setups.

It is desirable to have computed tomography scanning systems operate as fast as possible to maximize the number of patients that can be examined by a computed tomography scanner each working day and because the shorter time a scan takes, the easier it is for a patient to hold still during the scan. Further, the movement of internal organs is minimized.

As the scanning speed of a CT system is increased, the signal amplitude decreases for a fixed x-ray dose rate. Consequently, the signal-to-noise ratio, the contrast and thus the useful intensity resolution will decrease unless system parameters are adjusted to reduce noise. In order to reduce noise, the primary decay time of the scintillator should be reduced to a value where it does not contribute noise to the system. The afterglow should also be reduced as much as possible, since it provides a background luminescence intensity which is a noise contribution to the photodetector output. Selecting a scintillator material having its peak output in the vicinity of the peak sensitivity of the photodetector has the effect of reducing noise by increasing signal amplitude. Other modifications can also assist in maintaining the signal-to-noise ratio.

As the CT scanner field has matured, the speed of the electronics has increased, thus making faster scintillators desirable in order that a data scan may be performed in less time. It is now desired to operate CT scanning systems at speeds which require scintillators which are much faster than what was required as late as five years ago. Consequently, there is a vast lack of data about known solid luminescent materials which would be needed in order to select and make a scintillator material which is appropriate for use in a state-of-the-art CT scanning system where high speed electronics must be matched by a still higher speed scintillation material.

Separate from the problem of determining all these characteristics for individual candidate materials is the problem that, in a scintillation scanner, material must be provided in the form of a transparent solid body. Many luminescent materials which can be provided in powder form cannot be provided in a single crystalline form and thus are not available as transparent bodies. This inability to produce particular luminescent materials as single crystalline material can be a result of incompatibility of crystal structures, instability at Czochralski growth temperatures, low solubility of some components of a luminescent material in the crystal structure or the melt, a segregation coefficient which results in a non-uniform distribution within the boule of the additives and/or substituents or other reasons. Consequently, even if a particular luminescent composition is identified as apparently having desirable properties for use in a scintillation detector of a computed tomography-machine, production of such a scintillator detector is not straightforward. In many cases, the desired composition cannot be produced as a single crystalline material.

There are a number of luminescent materials which can be produced by flux growth techniques as small single crystals, but which cannot be produced as large single crystals because they are unstable at high temperatures and decompose into constituent materials. Other luminescent materials have been produced as thin films in attempts to develop phosphors for projection cathode ray tubes in order to minimize light loss due to scattering in amorphous or polycrystalline films. Such materials have no utility for the scintillators of CT scanners in the absence of an ability to provide a transparent body having sufficient thickness (generally at least 1 mm thick) for the material to be effective at stopping the x-rays employed in a CT scanning system. Further, the reports of the development work done on these materials contain no data on many characteristics which are crucial to determining whether a material is suitable for use in a CT scanning system.

A polycrystalline alternative to the single crystalline scintillator materials cesium iodide and cadmium tungstate is disclosed in U.S. Pat. Nos. 4,421,671; 4,466,929; 4,466,930; 4,473,413; 4,518,545; 4,518,546; 4,525,628; 4,571,312; 4,747,973 and 4,783,596. The scintillator composition disclosed in these patents is a cubic yttrium gadolinium oxide doped with various rare earth elements to provide a scintillator material having desired luminescent properties. These materials have not been prepared in single crystalline form because of the difficulty of growing crystals with desired, uniform distribution of all of the necessary constituents. As is further disclosed in the above recited patents, a method was developed for providing this doped yttrium-gadolinium oxide scintillator material in a polycrystalline ceramic form in which it is sufficiently transparent to provide an excellent scintillator material. This material has the substantial advantage over the cesium iodide and cadmium tungstate of being essentially free of radiation damage and hysteresis as well as having a sufficiently low afterglow to satisfy the requirements for a high quality CT scanning system. Unfortunately, this material has a primary decay time on the order of 1,000 microseconds and thus is not as fast as is desired for present state-of-the-art CT scanning systems.

It would be desirable to have a scintillator which is fast, has a low afterglow, no hysteresis, no non-linearity in output, high x-ray stopping power, high light output for a given stimulating x-ray input and which emits light at a frequency where photodetector diodes are particularly sensitive.

Single crystalline yttrium aluminum garnet (YAG) doped with neodymium is a known laser material. This material has also been further doped with chromium to increase the absorbence of the light frequency used to optically pump a YAG laser. While attempts have been made to produce transparent polycrystalline YAG, such attempts have not been successful. Reduced opacity or increased translucency or transparency has been reported in sintered YAG where magnesium oxide or silicon dioxide was included in the composition in a concentration of 500–2,000 ppm. However, even with this addition, true transparency is not obtained. Further, the inclusion of such transparency promoters in a scintillator material would be expected to be undesirable because of the potential for these impurities to adversely effect one or more of the desirable properties of a scintillator material.

Developments in optical and electrical ceramics have resulted in materials doped with multiple elements at 5 ppm to 1 mole percent levels. Dopants at such low levels can affect and improve the performance of these ceramics. Complex interactions between these elements makes optimization time consuming and expensive, as designs of experiments require dozens of individual samples, with each requiring a week of processing steps to form transparent samples for testing. Examples include the $Gd_3O_2S:Pr,F,Ce$ scintillator disclosed by Hitachi in U.S. Pat. No. 4,442,360, and the $Gd_3Ga_5O_{12}:Cr,Ce$ scintillator disclosed by GE in U.S. Pat. No. 5,484,750.

There thus exists a need for the development of a method of combinatorial chemistry, which has been previously used to develop thin-film materials such as phosphors, for developing scintillators from solid transparent materials having a general thickness of over 1 mm. Previous to the present invention, inorganic combinatorial chemistry did not generate transparent materials of this thickness. Transparency or translucency is an important parameter for many optical ceramics, and can influence the measurement and optimization of a host of other properties such as radiation damage of a scintillator. Transparency occurs when light freely passes through a material without optical attenuation, whereas translucency occurs when light passes through materials with an optical attenuation coefficient of less than about 100 cm$^{-1}$. A second limitation of the current state of the art is that of elemental doping levels. Parts per million levels can be used for controlling electronic and optical properties, and the thin film techniques developed to date are limited in doping levels due to volume considerations. This is because thin film techniques typically use evaporation methods, which makes it difficult to control dopants at the level of 10 to 100 ppm level. Techniques for the creation of transparent ceramic libraries (TCLs) will accelerate this process and will likely result in more highly optimized compositions of matter.

SUMMARY OF INVENTION

In a preferred embodiment of the present invention there is provided a method of preparing and testing an array of ceramics for optical properties, comprising: providing a host material that is capable of being made optically transparent or translucent upon sintering; forming the host material into an array of pixels attached to a base plate; doping the host material; reacting the host material and the dopant, to form an-array of products; and testing the products for optical properties.

BRIEF DESCRIPTION OF THE DRAWINGS

FIG. 2 is a pixel 3 wherein the top is shaped to be a vessel or well 4 that is capable of receiving a dopant solution.

DETAILED DESCRIPTION OF THE PREFERRED EMBODIMENTS

Figure 1:
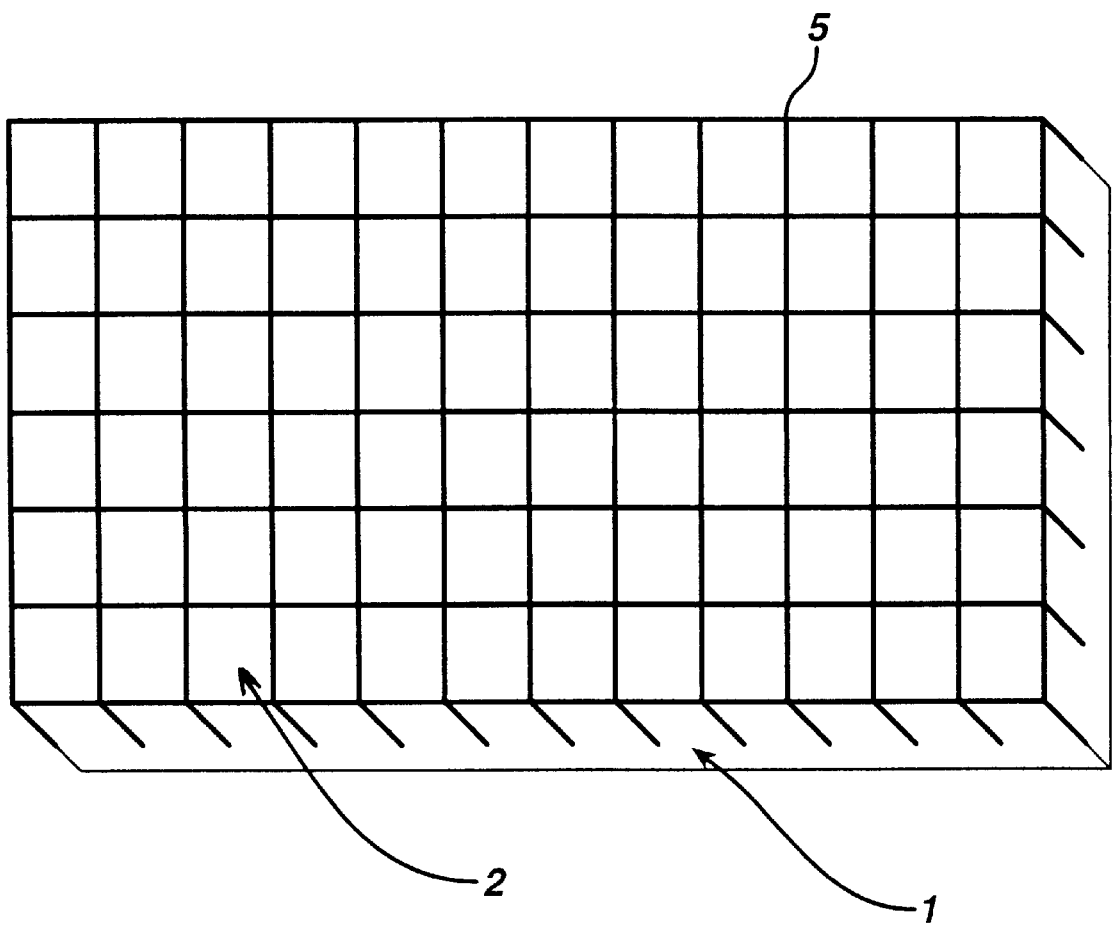
FIG. 1 shows a block of host material and that has been diced into individual pixels or sections, to which a dopant is added.

The preferred embodiments of the present invention provide methods for the preparation, measurement and use of scintillators using combinatorial techniques. The preferred embodiments of the present invention involve adding dopants to a host material, which can be any type of material suitable for use as scintillator. Such materials are preferably transparent or translucent polycrystalline materials. Examples of host materials are $Al_2O_3$, $Y_2O_3$, $SiO_2$, $Th_2O_3$, $Gd_2O_3$, oxide garnets such as $Gd_3Ga_5O_{12}$ and $Y_3Al_5O_{12}$, oxysulfides such as $Gd_2O_2S$, and salt solutions of $Y_2O_3$ and $Gd_2O_3$. Once dopants have chemically reacted with the host material, an array of products is formed and can be tested for properties that make the products useful as scintillators, such as short afterglow or persistance, low hysteresis, high x-ray stopping power, spectral linearity, high light output, etc. Accordingly, the dopants are preferably added to a single host material. By synthesizing an array of materials on a single host material, screening the array for materials having useful properties is more easily carried out. The host material, however, can already have dopant. In such a case, the dopant will be constant for the product library and dopant ions in addition to what is in the host material will be added.

Creation of a Library of Materials

An array of materials is prepared into a transparent ceramic library by successively delivering dopants of materials to predefined regions on a host material, and allowing the dopants and the host to chemically react to form at least two materials. In one embodiment, for example, a first dopant is delivered to a first region on a host material, and a second dopant is delivered to a second region on the host material. Optionally thereafter, additional dopants can be added to the predefined regions of the host material. The phrase plurality of materials or dopants means differing materials or the same material used in a differing amount or concentration. That is, each dopant can be delivered in either a uniform or gradient fashion to produce either a single stoichiometry or, alternatively, a large number of stoichiometries within each predefined region. After the dopants are added, they are reacted to form at least two materials. As previously mentioned, in addition to the combinatorially delivered dopants, one or more dopants may already be present in the host material.

Dopants are preferably ions added to the host material. The ions are generally added in the form of a precursor in a liquid solution. The dopants can be cationic or anionic, such as sulfur or phosphorous. Preferred dopants include transition metal ions such as Ti, Cr, Mn, Fe, Sr, Zr, Mo, Nd, Ba, Hf, Ta, and W and lanthanide ions such as Ce, Pr, Nd, Sm, Eu, Gd, Tb, Dy, Ho, Er, Tm, Yb, and Lu. Ionic dopants will have associated counter ions such as nitrate, acetate, bromide, chlorate, chloride, nitrate, salicylate, stearate, sulfate, or tartrate salt dissolved in water, alcohol, or mixture of water and alcohol.

Creation of the Host Material

The host material is preferably prepared and processed so that it will turn transparent or nearly transparent when the dopant is reacted with the host material. The skilled artisan will be able to select processes required to make the product transparent according to the starting host material. Examples of such processes include steps such as controlled co-precipitation of oxalate or chloride precursors, followed by drying, sieving, and milling of the precursor, calcining of the precursor into an oxide powder with proper powder morphology, and pressing the powder into a green block. These processes are well known in the art and have been taught, for example, in U.S. Pat. Nos. 4,242,221, 4,518,545 and 5,484,750. The steps should be taken through any final pressing that cannot be done after the blocks have been formed into a shape, as detailed below. The material at this stage should include the host material as well as any further dopant needed, preferably at levels at 10 mole percent or less.

Delivery of Dopants

The dopants in the individual reaction regions are preferably prevented from moving to adjacent reaction regions. This is easily accomplished by fabricating the host material into an array of pixels. In one approach, a host material is fabricated into a block and then diced into individual pixels 2 or sections, as in FIG. 1. Dicing is a well-known term of art that means cutting into something. Pixel is another well-known term of art that means a pillar-like protrusion of a base material. The pixel can be of many shapes, such as circular or polygonal, or of various dimensions, as long as the pixel is capable of receiving discrete amounts of dopant. Pixels preferrably are over about 10 microns in thickness, and in one preferred embodiment have a height of between about 100 microns to about 5 mm. Individual blocks for doping are connected to a base 1 of the host material. The blocks may be formed by dicing a single solid block with perpendicular grooves as in FIG. 1, or may be formed by injection molding of this shape from the powder. The injection molding or the gel/slip casting of the block of the host composition allows net shape fabrication of the pixelated structure. Standard practices of these fabrication methods can be employed that involve forming a moldable "paste" or castable slurry, with a suitable organic binder, and molding the slurry into a predesigned sacrificial mold. The molded part is then removed from the mold and heat treated to remove the binder. The plastic can be removed by burning or melting it off, as well as by physical means.

The pixels are preferably made to be at a height of about 0.1 mm or greater. As shown in FIG. 2, the tops of the pixels 3 may be shaped to be wells 4 that are capable of receiving the dopant solution, which is subsequently absorbed into the pixel by capillary action.

Doping the Individual Areas

Doping of the blocks is done by absorbing liquid media into the porous blocks. The porosity of the blocks is approximately from about 30 to about 70% at this stage, and capillarity action will drive the medium into the interstices between the ceramic grains. The medium may be water or an alcohol that can dissolve compounds used to dope the libraries. For example, for rare-earths an acetate, nitrate, sulfate, or chloride could be used, for transition metal ions an acetate, bromide, chlorate, chloride, nitrate, salicylate, stearate, sulfate, or tartrate salt may be dissolved in the medium. Combinations of dopant ions can be prepared using standard combinatorial chemistry techniques, and these combinations can be doped all at once into the individual blocks. Such types of dopant delivery mechanisms are well known in the art. Alternatively, the dopants can be added separately with or without a drying step (see step 4, below) between each addition. This solves the problem of separate additives being soluble in different or incompatible media. In either case, each block can then have a unique combination of host and added dopants, including varied concentration of dopants.

In the delivery systems of the preferred embodiments, a precisely quantified amount of each dopant is delivered into each reaction region. The skilled artisan will appreciate that this may be accomplished using a variety of well-known delivery techniques, either alone or in combination with a variety of masking techniques.

For example, the host material can be prefabricated as a single piece through well-known fabrication processes such as dry pressing of powders, injection molding, sequential screen printing, tapecasting sheets, lamination etc. This structure thus formed can then be separated into regions or arrays for the addition of the dopants by dicing them into individual pixels. Alternatively, the host material can be fabricated into a pixelated structure as shown in FIG. 1 via slip/gel casting a slurry of the required composition or injection molding. In FIG. 1, is a block of host material in which the pixels 1 protrude from a base material 2. In between the pixels 1 is a light blocking material 5. Alternatively, the host material can be delivered into the isolated cavities as a loose powder, a powder, or a slurry.

Dopants can be deposited into the reaction regions of interest from a dispenser in the form of droplets or powder by a variety of techniques well known in the art. These include a micropipetting apparatus or an ink-jet dispenser system, including a pulse pressure type dispenser system, the bubble jet type dispenser system and the slit jet type dispenser system. Such dispenser systems can be manual or, alternatively, they can be automated using, for example, robotics techniques.

A dispenser can be aligned with respect to the appropriate reaction regions by a variety of systems well known to those of skill in the art. Such systems, which are widely used in the microelectronic device fabrication and combinatorial arts, can deliver droplets to individual reaction regions at rates of up to 5,000 drops per second. The translational (X-Y) accuracy of such systems is well within 1 $\mu$m. The position of the dispenser stage of such systems can be calibrated with respect to the position of the host material by a variety of methods known in the art. For example, with only one or two reference points on the surface of, the array or host material, the reference marks in any such systems can be accurately identified by using capacitive, resistive or optical sensors. Alternatively, a system using a camera can be employed. In another embodiment of the present invention, the dispenser can be aligned with respect to the reaction region of interest by using a reaction region in which the dopant is to be deposited as identified by its track and sector location on a disk. The dispenser is then moved to the appropriate track while the disk rotates. When the appropriate reaction region is positioned below the dispenser, a droplet of reactant solution is released.

Evaporating the Dopant Medium

The solution used to deliver the dopant, such as water or alcohol, is preferably removed from the grain interstices of the host material by such processes as evaporation or freeze drying. A high temperature cycle up to 1000° in air or oxygen may be necessary to convert some of the dopants into oxides prior to the sintering step, especially if the sintering is done in reducing conditions such as wet or dry hydrogen. In any of these steps barriers such as metal foils or plates can be placed in the gaps between the blocks in order to minimize cross contamination between blocks. These barriers may be used during the evaporation step, the sintering step, or both. Flowing atmosphere over the foil will also serve to minimize cross contamination during evaporation. If multiple dopants are being added, drying steps between each addition can be used.

Sintering the Array Library to Transparency

Sintering procedures well known in the art can be followed to sinter the doped "green" library to transparency. As is well known in the art, parameters such as atmosphere, temperature and time are selected according to the type of material selected for sintering. For example, sintering at a temperature of between about 70% and 95% of the material's melting point in an oxygen or hydrogen atmosphere between about 1600° C. to about 1800° C. in oxygen for about 4 to about 24 hours. During this step the previously introduced dopants diffuse through and react with the host material.

Optically Isolating the Individual Areas of the Arrays

Following the sintering, the individual blocks can be optically isolated by introducing a scattering or absorbing media between the blocks. For example, an epoxy/$TiO_2$ composition can be cast in these gaps. In addition to providing optical isolation between the individually doped blocks, this material will hold the library together when the base is removed. Alternatively, prior to sintering, the gaps can be filled with a powder, which does not sinter to transparency. This can be a powder of host material that has a green density or particle size distribution that inhibits sintering to transparency. Such a green density is preferably less than 40% porosity and such a particle size distribution is from about 0.1 $\mu$m to about 100 $\mu$m. Also, metal foil or plates such as platinum or tungsten can be placed in the gaps during sinter to minimize cross contamination between the blocks. In addition, transparent epoxy can be used to hold the library together, particularly if pixels are analyzed individually.

Grinding Off the Base

After the array has been sintered to transparency, the base portion of the array is preferably removed. Up until the sintering step, the base serves to hold the individual areas of the host material together and acts as a reservoir for surplus buffer material, thus ensuring that the pixel is uniformly doped throughout. The base can be removed by dicing, grinding, polishing or lapping. Also, the top and or bottom of the surface of the library can be smoothed, so that light scattering is reduced or diminished. Either or both surfaces can be polished to evaluate transparency, grain structure, and scattering centers, and other optical properties such as absorption and luminescence.

The library can then be tested with an electromagnetic wavelength generating source. Examples of testing procedures include using a diode array, a laser beam or an optical beam to evaluate light output under an input of electromagnetic energy. For example, light output under x-ray or other excitation wavelength, can be evaluated for optical properties such as emission efficiency, turn-on delay, primary decay time, hysteresis, luminescent spectrum, afterglow, radiation damage, and pump-up.

These techniques can be used to develop advanced ceramic scintillators for medical and NDE applications and arc tubes for lighting applications.

We claim:

1. A method of preparing and testing an array of ceramics for optical properties, the method comprising:
   providing a block of the host material that is capable of being made optically transparent or translucent upon sintering;
   forming the block into an array of pixels;
   doping each of the pixels with at least a dopant;
   reacting the host material of each of the pixel with said at least a dopant to form an array of products;
   sintering the array of products to produce the array of ceramics; and
   testing the array of ceramics for the optical properties.

2. A method of claim 1, further comprising evaporating a doping medium prior to reacting the host material and the dopant.

3. A method of claim 1, wherein the host material is a powder.

4. A method of claim 3, wherein the host material is pressed into a shape prior to doping.

5. A method of claim 4, wherein the array of pixels is formed by dicing the host material shape above a base plate area.

6. A method of claim 3, wherein the array of pixels is formed by injection molding of the host material.

7. A method of claim 3, wherein the array of pixels is formed by pressing the powder into a sacrificial mold.

8. A method of claim 7, further comprising removing the sacrificial mold prior to reacting the host material.

9. A method of claim 8, wherein the sacrificial mold is removed by burning, evaporation or melting.

10. A method of claim 1, wherein the array of the host material has a porosity of from about 30% to about 70%.

11. A method of claim 1, further comprising removing the base from the pixels.

12. A method of claim 1, wherein the dopant is in the form of a precursor in a liquid solution.

13. A method of claim 12, wherein the dopant is a transition metal ion.

14. A method of claim 13, wherein the dopant is select from the group consisting of: Ti, Cr, Mn, Fe, Sr, Zr, Mo, Nd, Ba, Hf, Ta, and W.

15. A method of claim 12, wherein the dopant is a lanthanide.

16. A method of claim 15, wherein the dopant is select from the group consisting of: Ce, Pr, Nd, Sm, Eu, Gd, Tb, Dy, Ho, Er, Tm, Yb, and Lu.

17. A method of claim 12, wherein the dopant has a counter ion selected from the group consisting of: nitrate, acetate, bromide, chlorate, chloride, nitrate, salicylate, stearate, sulfate, or tartrate salt dissolved in water, alcohol, or a mixture of water and alcohol.

18. A method of claim 11, wherein more than one dopant is added.

19. A method of claim 18, wherein dopants are adding with drying steps between each addition.

20. A method of claim 11, wherein a solvent is removed prior to reacting the dopant and the host material.

21. A method of claim 20, wherein a solvent is removed by evaporation or freeze drying.

22. A method of claim 1, further comprising placing a metal foil or plate between the individual pixels prior to reacting the dopant and the host material.

23. A method of claim 1, further comprising flowing a gas over the host material and the dopants while they are being reacted.

24. A method of claim 1, further comprising removing the base from the array.

25. A method of claim 24, wherein the base is removed by dicing, grinding, polishing or lapping.

26. A method of claim 1, further comprising smoothing or polishing a surface of the array.

27. A method of claim 1, wherein the testing comprises supplying a laser beam, a diode array or an optical beam to evaluate light output under an input of electromagnetic energy.

28. A method of claim 27, wherein the electromagnetic energy input is an X-ray input.

29. A method of claim 28, wherein emission efficiency, afterglow, radiation damage or pump up is tested.

30. A method of claim 1, wherein the host material is $Al_2O_3$, $Y_2O_3$, $SiO_2$, $Th_2O_3$, $Gd_2O_3$, oxide garnets, $Gd_3Ga_5O_{12}$, and $Y_3Al_5O_{12}$, oxysulfides, $Gd_2O_2S$, and salt solutions of $Y_2O_3$ and $Gd_2O_3$.

31. A method of claim 1, wherein the dopant is delivered at a concentration of 10 mole percent or less in a doping medium.

32. A method of preparing and testing an array of ceramics for optical properties, comprising:
   providing a host material that is capable of being made optically transparent or translucent upon sintering;
   forming the host material into an array of pixels attached to a base plate;
   doping the host material with at least a dopant;
   reacting the host material and said at least a dopant, to form an array of products;
   placing a material between the pixels; and
   testing the products for optical properties.

33. A method of claim 32, wherein the material between the pixels is optically opaque or light scattering.

34. A method of claim 32, wherein the material between the pixels is transparent.

35. A method of preparing and testing an array of ceramic scintillators for optical properties, the method comprising:
   providing a block of the host material that is capable of being made optically transparent or translucent upon sintering;
   forming the block into an array of pixels;
   doping each of the pixels with at least a dopant;
   reacting the host material of each of the pixel with said at least a dopant to form an array of ceramic products;
   sintering the array of ceramic products to produce the array of ceramic scintillators; and
   testing the array of ceramic scintillators for the optical properties.

36. A method of preparing and testing an array of ceramic scintillators for optical properties, the method comprising:
   providing a block of the host material that is capable of being made optically transparent or translucent upon sintering, the block having a porosity;
   forming the block into an array of porous pixels;
   doping each of the porous pixels with at least a dopant by imbibing said at least a dopant thereinto;
   reacting the host material of each of the pixel with said at least a dopant to form an array of ceramic products;
   sintering the array of ceramic products to produce the array of ceramic scintillators; and
   testing the array of ceramic scintillators for the optical properties.

* * * * *